United States Patent
Schwager

[19]

[11] Patent Number: 5,836,885
[45] Date of Patent: Nov. 17, 1998

[54] PRESSURE MONITORING GUIDEWIRE AND METHOD FOR MANUFACTURING SAME

[75] Inventor: Michael Schwager, Winterthur, Switzerland

[73] Assignee: Schneider (Europe) AG, Bulach, Switzerland

[21] Appl. No.: 988,583

[22] Filed: Dec. 11, 1997

[30] Foreign Application Priority Data

May 21, 1997 [EP] European Pat. Off. .............. 97108245

[51] Int. Cl.[6] ................................................... A61M 5/00
[52] U.S. Cl. ............................................................ 600/486
[58] Field of Search .................................... 600/433, 434, 600/435, 466, 486, 487, 488, 585; 604/53, 280; 427/575

[56] References Cited

U.S. PATENT DOCUMENTS

| | | | |
|---|---|---|---|
| 4,003,369 | 1/1977 | Heilman et al. | 128/2 |
| 4,080,706 | 3/1978 | Heilman et al. | 29/173 |
| 4,721,117 | 1/1988 | Mar et al. | 128/772 |
| 4,724,846 | 2/1988 | Evans, III | 128/772 |
| 4,779,628 | 10/1988 | Machek | 128/772 |
| 4,854,330 | 8/1989 | Evans, III et al. | 128/772 |
| 4,895,168 | 1/1990 | Machek | 128/772 |
| 4,922,924 | 5/1990 | Gambale et al. | 128/772 |
| 4,953,553 | 9/1990 | Tremulis | 128/637 |
| 4,964,409 | 10/1990 | Tremulis | 128/657 |
| 4,971,490 | 11/1990 | Hawkins | 128/772 |
| 5,050,606 | 9/1991 | Tremulis | 128/637 |
| 5,063,935 | 11/1991 | Gambale | 128/657 |
| 5,069,226 | 12/1991 | Yamauchi et al. | 128/772 |
| 5,129,890 | 7/1992 | Bates et al. | 604/281 |
| 5,171,383 | 12/1992 | Sagaye et al. | 148/564 |
| 5,267,574 | 12/1993 | Viera et al. | 128/772 |
| 5,345,945 | 9/1994 | Hodgson et al. | 128/772 |
| 5,376,083 | 12/1994 | Mische | 604/264 |
| 5,380,307 | 1/1995 | Chee et al. | 604/264 |
| 5,404,886 | 4/1995 | Vance | 128/772 |
| 5,425,724 | 6/1995 | Akins | 604/284 |
| 5,429,139 | 7/1995 | Sauter | 128/772 |
| 5,458,585 | 10/1995 | Salmon et al. | 604/280 |
| 5,511,559 | 4/1996 | Vance | 128/772 |
| 5,523,126 | 6/1996 | Sano et al. | 427/575 |
| 5,527,292 | 6/1996 | Adams et al. | 604/171 |
| 5,527,298 | 6/1996 | Vance et al. | 604/280 |
| 5,569,197 | 10/1996 | Helmus et al. | 604/96 |
| 5,605,163 | 2/1997 | Hani | 128/772 |
| 5,617,875 | 4/1997 | Schwager | 128/772 |
| 6,127,917 | 7/1992 | Niederhauser et al. | 606/191 |

FOREIGN PATENT DOCUMENTS

| | | |
|---|---|---|
| 0313836 A3 | 5/1989 | European Pat. Off. . |
| 0405823 A2 | 1/1991 | European Pat. Off. . |
| 0652026 A1 | 5/1995 | European Pat. Off. . |
| 0729765 A1 | 9/1996 | European Pat. Off. . |
| 0738495 A1 | 10/1996 | European Pat. Off. . |
| 0750879 A1 | 1/1997 | European Pat. Off. . |

OTHER PUBLICATIONS

Search Report dated Nov. 6, 1997 in corresponding European Patent Application No. 97108245.8, together with Communication and one-page Annex.

U.S. application Serial No. 08/989,321, entitled "Controlled Gap Guidewire", filed Dec. 11, 1997, which is commonly-owned by the assignee of the above-captioned application.

U.S. application Serial No. 08/989,071, entitled "Slotted Pressure Monitoring Guidewire", filed Dec. 11, 1997, which is commonly-owned by the assignee of the above-captioned application.

*Primary Examiner*—George Manuel
*Attorney, Agent, or Firm*—Peter C. Richardson; Lawrence C. Akers; Philip C. Strassburger

[57] ABSTRACT

The pressure monitoring guidewire comprises an elongated tube made of one piece of elastic Nickel Titanium alloy. The distal end portion of the tube has transverse openings formed through the tube wall for the entry of pressure waves into a lumen. The distal end portion of the tube which encompasses the openings, is malleable. The pressure monitoring guidewire can be formed by thermally treating the distal end portion of a guidewire formed of an elongated tube of one piece of elastic Nickel Titanium alloy having a distal end portion with transverse openings.

5 Claims, 1 Drawing Sheet

PRESSURE MONITORING GUIDEWIRE AND METHOD FOR MANUFACTURING SAME

BACKGROUND OF THE INVENTION

This Application claims priority under 35 U.S.C. § 119 of European Patent Application No. 97108245.8 filed in the European Patent Office on May 21, 1997.

This invention relates to a pressure monitoring guidewire comprising an elongated tube made of one piece of elastic Nickel Titanium alloy having a distal end portion with transverse openings for the entry of pressure waves into the tube. The invention also relates to a method for manufacturing such a guidewire.

The monitoring of fluid pressures during intravascular procedures such as angioplasty, angiography of valvuloplasty, gives valuable information to the cardiologist to assess both coronary and myocardial flow reserve and collateral blood flow.

Attempts have been made to develop hollow guidewires which allow for the measurement of the fluid pressure at the distal end of a catheter from the proximal end thereof. Such guidewires comprise a plurality of side openings in the distal portion of the tubular shaft to allow blood pressure waves to propagate to a pressure sensor connected to the proximal portion of the shaft. A problem with such pressure monitoring guidewires is to provide an uninterrupted lumen throughout the shaft which has to be highly flexible to conform with tortuous pathways of the blood vessels. However, the shaft must also have a reasonably high stiffness to assure pushability and torque transmission thereto. And furthermore, the shaft must have a good kink resistance to avoid the risk of constrictions which would affect the advance of pressure waves through the lumen.

Pressure monitoring guidewires have been made of an elongated tube made of one piece of elastic material, preferably a superelastic Nickel Titanium alloy, with transverse openings at a distal end portion thereof for the entry of pressure waves into the tube. That kind of pressure monitoring guidewires avoids the connection of different materials for making the tube, and provides a good flexibility, with the required stiffness for pushability and torque transmission and kink resistance, but the difficulty is that the transverse openings result in a weakening in the cross-section of the bent tube, which causes a high potential of kinking in the area provided with the openings. Kinking occurs when the cross-section of the bent tube undergoes a drastic deformation which results in a constriction of the inner lumen by folding of the inner wall of the tube. In other words, the tube tends to bend back upon itself and such a situation particularly occurs when attempting to pass the guidewire through a calcified lesion, or a mostly occluded vessel section, or still a very tortuous vascular section. Once kinking occurs, pressure wave signals are strongly affected and the guidewire has to be discarded because it cannot be adequately straightened, either because of the deformation or because the cardiologist can usually not spend time to attempt to straighten the kinked guidewire. Consequently, the vascular procedure has to be interrupted and a new pressure monitoring guidewire selected, reinserted and manipulated to be advanced to the target site. This of course increases the risk of trauma to the blood vessel.

EP 0 738 495 A1 shows a pressure measuring guidewire as referred to hereinabove. The pressure measuring guidewire comprises an elongated tubular shaft made of an elastic Nickel Titanium alloy the distal area of which comprises a plurality of transverse elongated slots formed in the tubular shaft wall for pressure medium entry, whereby the resistance to kinking of that area of the shaft differs from that of the proximal area of the shaft which is devoid of slots. In one embodiment, the wall forming the shaft has at the location of the slots a greater thickness than the thickness at the proximal area of the shaft to compensate the difference in kinking resistance between proximal and distal areas of the shaft. In another embodiment, the wall forming the shaft has the same thickness at the location of the slots and at the proximal area of the shaft, and a coil is located inside the shaft under the slots for supporting the slotted wall and thereby compensating for the difference in kink resistance between the slotted portion of the shaft and the portion thereof which is devoid of slots; a core member is located within the coil with proximal and distal ends formed to abut longitudinally with the corresponding ends of the coil in order to stiffen the coil. In a variant, the core member may have its proximal end extended by a wire which goes proximally along and out of the lumen of the shaft, whereby the coil may be placed under the slots only for insertion of the guidewire to assure resistance to kinking of the slotted area, and when the guidewire is properly located the supporting coil may be withdrawn out of the guidewire by pulling the core in order to maintain the shaft lumen free of obstructions for pressure measurements.

EP 0 750 879 A1 also shows a pressure measuring guidewire made of an elongated tubular shaft made of an elastic Nickel Titanium alloy. The distal area of the tubular shaft is provided with transverse slots for pressure medium entry into the lumen of the shaft. A stiffening means formed by an independent wire removably extends through the lumen of the shaft and proximally of the proximal area of the shaft. Accordingly, the shaft may be devised as a tubing with extremely thin walls the flexibility and floppiness and resistance to kinking of which can be selected at will, and the independent wire may be withdrawn from the shaft for pressure measurements to take advantage of a lumen free of any obstruction.

All documents cited herein, including the foregoing, are incorporated herein by reference in their entireties for all purposes.

SUMMARY OF THE INVENTION

It is an object of this invention to propose a pressure monitoring guidewire which is easy and inexpensive to manufacture while having excellent qualities of pushability and resistance to kinking, and which allows a smooth advance of pressure waves in a very low profile guidewire configuration.

Still a further object of the invention is a method for manufacturing the pressure monitoring guidewire which is easy to implement and fully controllable.

Accordingly, when a pressure monitoring guidewire comprising an elongated tube made of one piece of elastic Nickel Titanium alloy having a distal end portion with transverse openings for the entry of pressure waves into the tube is characterized in that said distal end portion of the tube is more malleable than an adjacent portion of the tube, the weakening effect on the tube resulting from the transverse openings is largely compensated. The distal end portion of the tube is more capable of undergoing plastic deformation without rupture and, therefore it can be bent along a very small bending radius without constricting the inner lumen by folding of the inner wall of the tube. As the tube is stressed by bending, the pliable material deforms smoothly rather than building up peak stresses, the risk of kinking at the openings area becomes remote and the pressure monitoring guidewire may make its way through calcified lesions or mostly occluded vessel sections or still very tortuous vascular sections. The elongated tube retains a very high flexibility at any location provided with openings. There is no more need for wall overthickness or for wall supporting cores or coils to compensate a loss of resistance to kinking due to pressure waves entry openings and there are no transitions or obstructions within the lumen of the tube which would interfere on the passage of fluid pressure pulses. The pressure monitoring guidewire allows the passage of strong detectable signals, even when the pressure monitoring guidewire has a very low wall and profile configuration.

The malleable portion of the tube may have an outer diameter reduced with respect to a portion of the tube immediately proximal thereto to further raise bendability at the area of the transverse openings towards reaching very narrow and tortuous vessel configurations.

When the reduced diameter portion joins gradually the portion of the tube immediately proximal thereto, flexibility increases stepwise at the transition of the two diameters of the tube.

By the steps of forming an elongated tube of one piece of elastic Nickel Titanium alloy having a distal end portion with transverse openings and thermally treating said distal end portion of the tube, the critical stress that triggers a material rupture is shifted. The strain at which rupture occurs increases and, therefore, the distal end portion of the tube can be bent according to a smaller radius. As a result, the phenomenon of kinking becomes remote.

Preferably, the distal end portion of the tube is treated at about 450° C. during at least a quarter of an hour, which is easy to achieve and control with available equipment.

In sum, the invention relates to a pressure monitoring guidewire including an elongated tube made of one piece of elastic Nickel Titanium alloy having a distal end portion with transverse openings for the entry of pressure waves into the tube. The distal end portion of the tube is more malleable than an adjacent portion of the tube. The malleable portion of the tube may have an outer diameter reduced with respect to a portion of the tube immediately proximal thereto. The reduced diameter portion may join gradually the portion of the tube immediately proximal thereto. A method for manufacturing the guidewire may include the steps of forming an elongated tube of one piece of elastic Nickel Titanium alloy having a distal end portion with transverse openings, and thermally treating the distal end portion of the tube. The method may include the distal end portion of the tube being thermally treated at about 450° C. during at least a quarter of an hour.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

Figure 1:
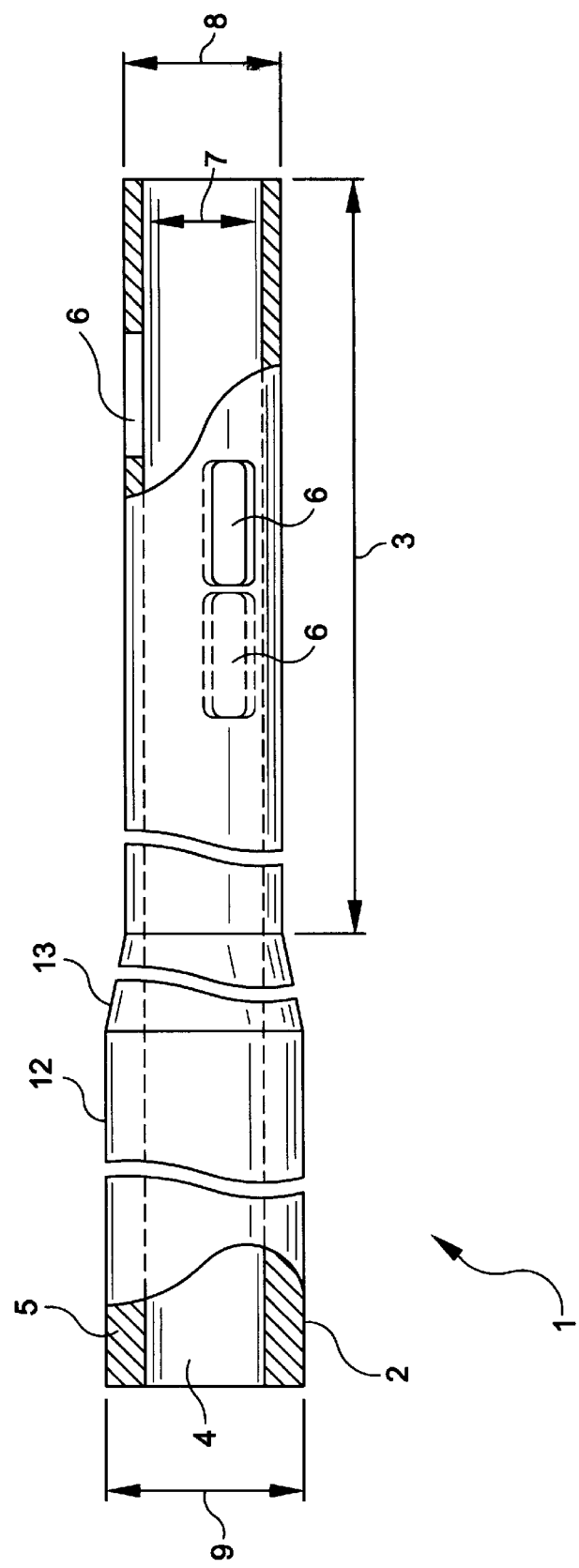
FIG. 1 is a fragmentary centerline sectional view of the tubular shaft of a pressure monitoring guidewire according to the invention.

The pressure monitoring guidewire shown in FIG. 1 comprises an elongated tube 1 made of one piece of elastic Nickel Titanium alloy. The tube 1 has a proximal end portion 2 and a distal end portion 3.

A lumen 4 extends through the tube 1 and the proximal end portion 2 is intended to be connected to a pressure measuring equipment (not shown) as common in the art. The lumen 4 is defined by the wall 5 of the tube 1.

The distal end portion 3 of the tube 1 has three transverse openings 6 formed therein through the wall 5 for the entry of pressure waves into lumen 4. The transverse openings 6, in the form of elongated slots, are distributed along a helical path by 120° shifts in the transverse direction 7.

The distal end portion 3 of the tube 1 is for termination into a flexible tip assembly (not shown), for example as shown in EP 0 738 495 A1. the distal end portion 3 of tube 1, which encompasses the openings 6, is malleable.

The malleable portion 3 of the tube 1 has an outer diameter 8 which is reduced with respect to the outer diameter 9 of the portion 12 of tube 1 immediately proximal thereto. Junction of reduced diameter portion 3 to larger diameter portion 12 is effected gradually by a frustum 13.

Advantageously, the manufacturing of the pressure monitoring guidewire I may be obtained by forming the elongated tube 1 of one piece of elastic Nickel Titanium alloy having the distal end portion 3 with transverse openings 6, and thermally treating the distal end portion 3 of tube 1.

The thermal treatment may be achieved in an oven (not shown) and, preferably, the thermal treatment will be at about 450° C. during at least a quarter of an hour.

Variants are available. For example, the openings 6 may be different in shape and geometrical arrangement. Malleability may be extended proximally of the distal end portion 3 of tube 1, whereas thermal treatment will be extended accordingly. Duration and timing of the thermal treatment may be different.

The reduced diameter configuration may be not be limited to the malleable portion of the tube. Similarly, the malleable portion of the tube may have the same diameter as the proximal portion of the tube.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A pressure monitoring guidewire comprising:
   an elongated tube made of one piece of elastic Nickel Titanium alloy having a distal end portion with transverse openings for the entry of pressure waves into the tube wherein the distal end portion of the tube is more malleable than an adjacent portion of the tube.

2. A pressure monitoring guidewire according to claim 1 wherein the malleable portion of the tube has an outer diameter reduced with respect to a portion of the tube immediately proximal thereto.

3. A pressure monitoring guidewire according to claim 2 wherein the reduced diameter portion joins gradually the portion of the tube immediately proximal thereto.

4. A method for manufacturing the guidewire according to claim 1 comprising the steps of forming an elongated tube of one piece of elastic Nickel Titanium alloy having a distal end portion with transverse openings and thermally treating the distal end portion of the tube.

5. A method according to claim 4 wherein the distal end portion of the tube is thermally treated at about 450° C. for at least 15 minutes.

* * * * *